(12) United States Patent
Ogasawara et al.

(10) Patent No.: US 12,412,322 B2
(45) Date of Patent: Sep. 9, 2025

(54) X-RAY DIAGNOSTIC APPARATUS CAUSES X-RAY DETECTOR TO READ A SIGNAL IN NON-DESTRUCTIVE READOUT AND TO READ A SIGNAL IN DESTRUCTIVE READOUT AND GENERATES FIRST AND SECOND PROJECTIONS DATA, AND NON-TRANSITORY COMPUTER-READABLE STORAGE MEDIUM

(71) Applicant: Canon Medical Systems Corporation, Otawara (JP)

(72) Inventors: Jumpei Ogasawara, Nasushiobara (JP); Kunio Shiraishi, Otawara (JP); Hajime Yoshida, Nasushiobara (JP); Akihito Takahashi, Nasushiobara (JP); Yasuto Hayatsu, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 356 days.

(21) Appl. No.: 18/191,166

(22) Filed: Mar. 28, 2023

(65) Prior Publication Data
US 2023/0351647 A1 Nov. 2, 2023

(30) Foreign Application Priority Data
Mar. 30, 2022 (JP) ................. 2022-056440

(51) Int. Cl.
 *A61B 6/00* (2024.01)
 *G06T 11/00* (2006.01)
(52) U.S. Cl.
 CPC .......... *G06T 11/005* (2013.01); *A61B 6/4441* (2013.01); *G06T 2207/10116* (2013.01); *G06T 2210/41* (2013.01)

(58) Field of Classification Search
None
See application file for complete search history.

(56) References Cited

U.S. PATENT DOCUMENTS 10,677,939 B2 * 6/2020 Jacob ................... H04N 5/3205
10,924,687 B2 2/2021 Darson et al.
(Continued)

FOREIGN PATENT DOCUMENTS

| JP | 2005-204810 A | 8/2005 |
| JP | 2020-54760 A | 4/2020 |
| WO | WO 2013/065515 A1 | 5/2013 |

OTHER PUBLICATIONS

Extended European Search Report issued Aug. 22, 2023 in European Patent Application No. 23164615.9, 8 pages.

*Primary Examiner* — Haris Sabah
(74) *Attorney, Agent, or Firm* — Oblon, McClelland, Maier &Neustadt, L.L.P.

(57) ABSTRACT

According to one embodiment, an X-ray diagnostic apparatus including processing circuitry. The processing circuitry is configured to cause an X-ray detector to read a signal in a non-destructive readout before termination of X-ray exposure, the signal being accumulated in an X-ray detection element; cause the X-ray detector to read the signal in a destructive readout after termination of X-ray exposure; acquire first projection data generated based on the signal read in the non-destructive readout and acquire second projection data generated based on the signal read in the destructive readout; estimate, based on the second projection data, a saturation region in which saturation is occurring; and replace a signal in the saturation region of the second projection data with a signal in the saturation region of the first projection data.

20 Claims, 7 Drawing Sheets

(56) References Cited

U.S. PATENT DOCUMENTS

| | | | |
|---|---|---|---|
| 2004/0234032 A1 | 11/2004 | Nokita | |
| 2011/0051895 A1* | 3/2011 | Vogtmeier | A61B 6/4021 |
| | | | 378/92 |
| 2014/0219422 A1 | 8/2014 | Nishino et al. | |
| 2015/0371414 A1* | 12/2015 | Choi | G01N 23/04 |
| | | | 382/131 |
| 2017/0123079 A1 | 5/2017 | Jacob et al. | |
| 2021/0052236 A1* | 2/2021 | Nakai | G06N 5/04 |

* cited by examiner

X-RAY DIAGNOSTIC APPARATUS CAUSES X-RAY DETECTOR TO READ A SIGNAL IN NON-DESTRUCTIVE READOUT AND TO READ A SIGNAL IN DESTRUCTIVE READOUT AND GENERATES FIRST AND SECOND PROJECTIONS DATA, AND NON-TRANSITORY COMPUTER-READABLE STORAGE MEDIUM

CROSS-REFERENCE TO RELATED APPLICATION(S)

This application is based upon and claims the benefit of priority from Japanese Patent Application No. 2022-056440, filed Mar. 30, 2022, the entire contents of which are incorporated herein by reference.

FIELD

Embodiments described herein relate generally to an X-ray diagnostic apparatus, a medical image processing apparatus, and a storage medium.

BACKGROUND

The X-ray diagnostic apparatus uses an X-ray detector (FPD) for carrying out X-ray pulse irradiation and reading an image. For example, electric charge signals accumulated in the X-ray detector are read between pulses of X-rays emitted intermittently, and an X-ray image is produced based on the read electric charge signals.

Such an X-ray diagnostic apparatus may cause saturation because if the X-ray detector receives direct rays, the dose of X-rays incident upon the X-ray detector will exceed a maximum incident dose of the X-ray detector. If saturation occurs, a correct signal value cannot be read from the X-ray detector. Thus, an X-ray image generated cannot have a correct pixel value, likely causing artifacts in the generated X-ray image. As a method to solve this problem, there is known a method in which a signal value in a saturation region is estimated and saturation correction is performed. Such a method entails difficulty in accurately estimating the incident dose in the saturation region and making a correction.

SUMMARY

An X-ray diagnostic apparatus including: a first readout unit configured to cause an X-ray detector to read, in a non-destructive readout before termination of X-ray exposure, a signal accumulated in an X-ray detection element; a second readout unit configured to cause the X-ray detector to read the signal in a destructive readout after termination of X-ray exposure; an acquisition unit configured to acquire first projection data generated based on the signal read in the non-destructive readout and acquire second projection data generated based on the signal read in the destructive readout; an estimation unit configured to estimate a saturation region in which saturation is occurring based on the second projection data; and a correction unit configured to replace a signal in the saturation region of the second projection data with a signal in the saturation region of the first projection data.

A non-transitory computer-readable storage medium storing a program for causing a computer to execute: a function to cause an X-ray detector to read, in a non-destructive readout, a signal accumulated in an X-ray detection element before termination of X-ray exposure; a function to cause the X-ray detector to read the signal in a destructive readout after termination of X-ray exposure; a function to acquire first projection data generated based on the signal read in the non-destructive readout and acquire second projection data generated based on the signal read in the destructive readout; a function to estimate a saturation region in which saturation is occurring based on the second projection data; and a function to replace a signal in the saturation region of the second projection data with a signal in the saturation region of the first projection data.

The correction unit may replace the signal of the second projection data in a state where an image level of the first projection data and an image level of the second projection data are aligned with each other.

The correction unit may align the image level of the first projection data with the image level of the second projection data by converting an X-ray attenuation rate of the first projection data.

The correction unit may align the image level of the first projection data with the image level of the second projection data by calculating an X-ray attenuation rate of the second projection data using an air acquisition image generated by performing non-destructive readout in the absence of a subject.

The correction unit may align the image level of the first projection data with the image level of the second projection data by converting the image level of the first projection data.

The correction unit may align the image level of the first projection data with the image level of the second projection data using a ratio between the image level of the first projection data and the image level of the second projection data.

The correction unit may align the image level of the first projection data with the image level of the second projection data using a ratio between an X-ray accumulation time required when reading the first projection data and an X-ray accumulation time required when reading the second projection data.

The correction unit may divide the saturation region into a plurality of regions having different readout timings and align the image level of the first projection data with the image level of the second projection data for each of the regions.

The first readout unit may perform the non-destructive readout at each of a first readout time and a second readout time following the first readout time, and a central time between the first readout time and the second readout time may coincide with a central time between a time of performing readout with the second readout unit and a time of starting X-ray exposure.

The estimation unit may further estimate a non-saturation region in which no saturation is occurring based on the first projection data, and the correction unit may replace a signal near a boundary between the saturation region and the non-saturation region of the second projection data with a signal obtained by combining a signal of the first projection data with a signal of the second projection data.

The correction unit may change, according to a distance from the boundary, a ratio at which the signal of the first projection data is combined with the signal of the second projection data.

The X-ray diagnostic apparatus may further include a reconstruction processing unit configured to perform reconstruction processing on the replaced second projection data and generate three-dimensional image data.

The X-ray diagnostic apparatus may further include a support arm configured to hold an X-ray tube configured to emit X-rays and the X-ray detector. The acquisition unit may acquire the first projection data and the second projection data sequentially acquired while the X-ray detector is rotated around a subject by the support arm. The correction unit may replace a signal in the saturation region of the second projection data with a signal in the saturation region of the first projection data for each rotational angle of the support arm.

The timing before the termination of X-ray exposure may be a timing during singe pulse-irradiation.

The timing after the termination of X-ray exposure may be a timing after a single pulse-irradiation and between multiple pulse-irradiations.

BRIEF DESCRIPTION OF THE DRAWING(S)

DETAILED DESCRIPTION

An object is to generate a medical image in which artifacts caused by saturation are reduced. In general, according to one embodiment, an X-ray diagnostic apparatus including processing circuitry. The processing circuitry is configured to cause an X-ray detector to read a signal in a non-destructive readout before termination of X-ray exposure, the signal being accumulated in an X-ray detection element; cause the X-ray detector to read the signal in a destructive readout after termination of X-ray exposure; acquire first projection data generated based on the signal read in the non-destructive readout and acquire second projection data generated based on the signal read in the destructive readout; estimate, based on the second projection data, a saturation region in which saturation is occurring; and replace a signal in the saturation region of the second projection data with a signal in the saturation region of the first projection data.

Hereinafter, embodiments of an X-ray diagnostic apparatus and a medical image processing apparatus will be described in detail with reference to the accompanying drawings. In the description below, constituents having substantially the same functions and configurations will be denoted by the same reference symbols, and a repeat description of such constituents will be given only where necessary.

Embodiment

Figure 1:
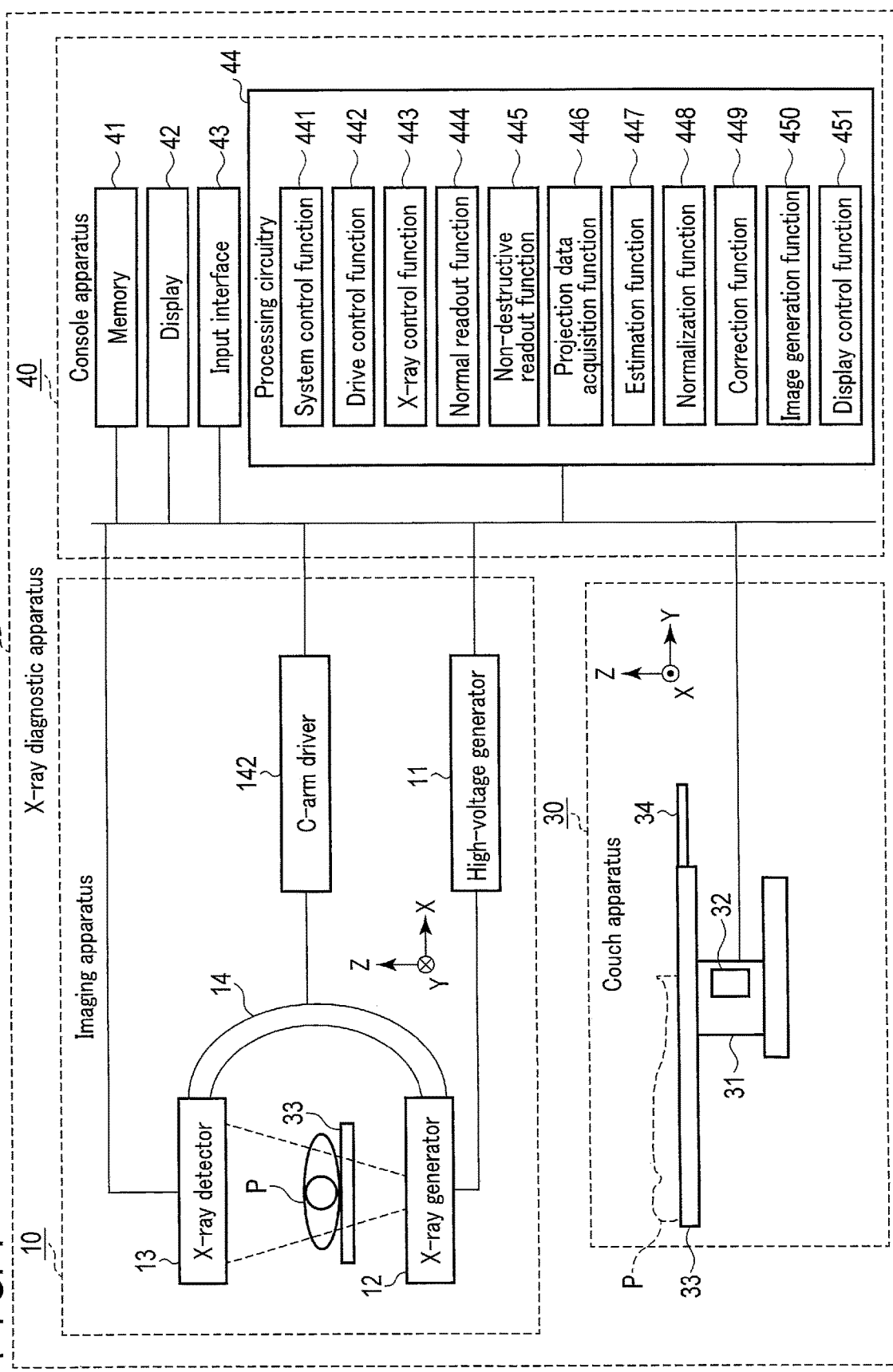
FIG. 1 is a diagram showing an example of a configuration of an X-ray diagnostic apparatus according to an embodiment.

FIG. 1 is a diagram showing an example of a configuration of an X-ray diagnostic apparatus 1 according to an embodiment. As shown in FIG. 1, the X-ray diagnostic apparatus 1 includes an imaging apparatus 10, a couch apparatus 30, and a console apparatus 40. The imaging apparatus 10 includes a high-voltage generator 11, an X-ray generator 12, an X-ray detector 13, a C-arm 14, and a C-arm driver 142. The X-ray diagnostic apparatus 1 is a cone-beam CT apparatus (CBCT apparatus) which emits X-rays in a cone-beam shape having a predetermined width in the body axis direction of a subject P.

The high-voltage generator 11 generates a high voltage to be applied between an anode and a cathode, and outputs the high voltage to an X-ray tube, so that thermoelectrons generated from the cathode of the X-ray tube are accelerated.

The X-ray generator 12 includes an X-ray tube that irradiates a subject P with X-rays, a plurality of filters having a function of attenuating or reducing an amount of X-rays emitted (hereinafter referred to as "added filters"), and an X-ray diaphragm. The X-ray generator 12 emits X-rays in a cone-beam shape having a predetermined width in the body axis direction of a subject P.

The X-ray tube is a vacuum tube that generates X-rays. The X-ray tube includes a tube bulb, a filament (cathode) provided on the tube bulb, and a tungsten anode. The X-ray tube accelerates the thermoelectrons released from the filament with the high voltage. The X-ray tube generates X-rays by making the accelerated electrons collide with the tungsten anode. The X-ray tube is a vacuum tube that generates X-rays in a cone-beam shape having a cone-shaped or pyramid-shaped expansion along the body axis direction of a subject P.

The X-ray diaphragm is located between the X-ray tube and the X-ray detector 13, and is made of a lead plate serving as a metal plate. The X-ray diaphragm limits the X-rays generated by the X-ray tube by blocking the X-rays outside an opening area, so that only a region of interest of the subject P is irradiated with the X-rays. In this manner, the size of an X-ray irradiation area (i.e., X-ray irradiation field) (hereinafter, referred to as a "field-of-view size") is adjusted. For example, the X-ray diaphragm includes four diaphragm blades, and slides these diaphragm blades to adjust the X-ray shield area into a desired size and thereby adjust the field-of-view size. The diaphragm blades of the X-ray diaphragm are driven by a driver (not shown) according to the region of interest input by an operator through the input interface 43.

The X-ray detector 13 detects X-rays that have been emitted from the X-ray tube and have passed through the subject P. As such an X-ray detector 13, both an X-ray detector configured to directly convert X-rays into electric charge and an X-ray detector configured to convert X-rays into light and then into electric charge can be used. The description below will take the former type of X-ray detector as an example of the X-ray detector 13, but the X-ray detector 13 may also be the latter type of X-ray detector. Specifically, the X-ray detector 13 includes, for example, a flat panel detector (FPD) that converts the X-rays that have passed through the subject P into electric charge and accumulates the electric charge, and a gate driver that generates drive pulses for reading the electric charge accumulated in the FPD. The FPD is constituted by micro detection elements arranged two-dimensionally in a row direction and a line direction. Each of the detection elements includes a photoelectric film that senses X-rays and generates electric charge according to an amount of incident X-rays, an electric-charge accumulating capacitor that accumulates electric charge generated on the photoelectric film, and a TFT (thin-film transistor) that outputs, at a predetermined timing, the electric charge accumulated on the electric-charge accumulating capacitor. The accumulated electric charge is sequentially read with the drive pulses supplied from the gate driver. The X-ray detector 13 is an example of an X-ray detector. Projection data generator circuitry (not shown) is arranged posterior to the X-ray detector 13. The projection data generator circuitry includes a parallel-serial converter that converts, into time-series serial signals (time-series projection data), digital signals read from the FPD of the X-ray detector 13 in parallel for each line and row. Time-series projection data is output from the projection data generator circuitry and supplied to the console apparatus 40.

In the present embodiment, a detector capable of performing both destructive readout and non-destructive readout is used as the X-ray detector 13. A destructive readout method is a method in which signals accumulated in the X-ray detection elements constituted by semiconductor devices such as photodiodes are forwarded to an integrating amplifier through a signal line and output signals corresponding to the signals integrated by the integrating amplifier are read. This method is referred to as "destructive readout" since the signals in the semiconductor devices are erased due to the forwarding of the signals. On the other hand, a non-destructive readout method is a method in which, with an amplifier for converting signals to output signals arranged in each semiconductor device, the output signals corresponding to the accumulated signals are read while the signals are retained in the X-ray detection elements. This method is referred to as "non-destructive readout" since the signals accumulated in the X-ray detection elements are retained without being erased even after the signals are read. In the present embodiment, a destructive readout function that the X-ray detector 13 has as a default function and that is performed after termination of X-ray irradiation is referred to as a "normal readout function".

The C-arm 14 is configured to hold the X-ray generator 12 and the X-ray detector 13 and carry out X-ray imaging while rotating. The C-arm 14 has a structure that enables X-ray imaging of the subject P lying on the top plate 33 to be performed by holding the X-ray generator 12 and the X-ray detector 13 in such a manner that they are opposed to each other with the subject P and the top plate 33 interposed therebetween. The C-arm 14 is supported slidably and rotatably about each of the rotation axes. The C-arm 14 is provided with a plurality of power sources for implementing the sliding and rotating operations that are arranged at suitable locations. These power sources constitute the C-arm driver 142. The C-arm driver 142 reads drive signals from a drive control function 442 to cause the C-arm 14 to slide, rotate, and move linearly. The C-arm 14 is an example of a support arm.

The couch apparatus 30 is an apparatus to place the subject P thereon and to move the subject P, and includes a base 31, a couch driver 32, a top plate 33, and a support frame 34.

The base 31 is a housing that is placed on the floor and supports the support frame 34 movably in the vertical direction (Z-axis direction).

The couch driver 32 is a motor or actuator that is accommodated in the housing of the couch apparatus 30 and moves the top plate 33 on which the subject P is placed in the longitudinal direction of the top plate 33 (Y-axis direction). The couch driver 32 reads drive signals from the drive control function 442 and moves the top plate 33 in a horizontal direction or a vertical direction with respect to the floor. The positional relationship between the subject P and the imaging axis changes when the C-arm 14 or the top plate 33 moves. The couch driver 32 may move not only the top plate 33 but also the support frame 34 in the longitudinal direction of the top plate 33.

The top plate 33 is a plate provided on the top surface of the support frame 34 and on which the subject P is placed.

The support frame 34 is provided above the base 31 and slidably supports the top plate 33 along its longitudinal direction.

The couch apparatus 30 may be configured so that the top plate 33 is movable with respect to the support frame 34 or the top plate 33 and the support frame 34 are movable together with respect to the base 31.

The console apparatus 40 includes a memory 41, a display 42, an input interface 43, and processing circuitry 44. The console apparatus 40 is described as an apparatus separate from the imaging apparatus 10; however, the console apparatus 40 or some of the constituents of the console apparatus 40 may be included in the imaging apparatus 10. For example, the console apparatus 40 corresponds to a medical image processing apparatus.

Hereinafter, the console apparatus 40 will be described as an apparatus performing a plurality of functions with a single console; however, a plurality of functions may be performed by separate consoles. For example, the functions of the processing circuitry 44, such as an image generation function 450 (described later), may be installed dispersively in different console apparatuses.

The memory 41 is a storage device, such as an HDD (hard disk drive), an SSD (solid state drive), or an integrated circuit, which stores various types of information. Other than being an HDD, an SSD, or the like, the memory 41 may be a portable storage medium such as a CD (compact disc), a DVD (digital versatile disc), or a flash memory. Alternatively, the memory 41 may be a driver that reads and writes various types of information from and in, for example, a semiconductor memory device such as a flash memory or a RAM (random access memory). The storage area of the memory 41 may be in the console apparatus 40 or in an external storage device connected via a network.

The memory 41 stores programs to be executed by the processing circuitry 44, various types of data to be used in the processing performed by the processing circuitry 44, and the like. Such programs include, for example, a program that is installed in a computer in advance via a network or a non-transitory computer-readable storage medium to cause the computer to implement each function of the processing circuitry 44. The various types of data as used herein are typically digital data. The memory 41 is an example of a storage unit.

The display 42 displays various types of information. For example, the display 42 outputs a medical image (an X-ray image) generated by the processing circuitry 44, a GUI (graphical user interface) for receiving various operations from an operator, and the like. For example, the display 42 is a liquid crystal display or a CRT (cathode ray tube) display. The display 42 may be provided on the imaging apparatus 10. Also, the display 42 may be a desktop-type display, or may be configured by a tablet terminal or the like capable of performing wireless communication with the main body of the console apparatus 40. The display 42 is an example of a display unit.

The input interface 43 receives various input operations from an operator, converts the received input operations into electric signals, and outputs the electric signals to the processing circuitry 44. For example, the input interface 43 receives scanning conditions for acquiring projection data, reconstruction conditions, instructions for moving the C-arm 14, setting of a region of interest (ROI), operations for performing fluoroscopy, and the like from an operator. For example, the input interface 43 is implemented by a mouse, a keyboard, a trackball, a switch button, a joystick, a touch screen in which a display screen and a touch pad are integrated, non-contact input circuitry that uses an optical sensor, audio input circuitry, etc., for performing various types of processing and the like of the processing circuitry 44. The input interface 43 is connected to the processing circuitry 44 and converts the input operations received from the operator into electric signals to output the electric signals to the control circuitry. In the disclosure made herein, the input interface is not limited to physical operating components such as a mouse and a keyboard. Examples of the input interface include processing circuitry for electric signals, which receives an electric signal corresponding to an input operation through an external input device separate from its own apparatus, and outputs this electric signal to the processing circuitry 44. The input interface 43 may be provided in the imaging apparatus 10 and may be constituted by, for example, a tablet terminal capable of performing wireless communication with the main body of the console apparatus 40. The input interface 43 is an example of an input unit.

The processing circuitry 44 controls the entire operation of the X-ray diagnostic apparatus 1. The processing circuitry 44 is a processor that invokes programs in the memory 41 and thereby performs a system control function 441, a drive control function 442, an X-ray control function 443, a normal readout function 444, a non-destructive readout function 445, a projection data acquisition function 446, an estimation function 447, a normalization function 448, a correction function 449, an image generation function 450, and a display control function 451.

Although FIG. 1 describes an instance in which single processing circuitry 44 performs the system control function 441, the drive control function 442, the X-ray control function 443, the normal readout function 444, the non-destructive readout function 445, the projection data acquisition function 446, the estimation function 447, the normalization function 448, the correction function 449, the image generation function 450, and the display control function 451, the embodiment is not limited thereto. For example, a plurality of independent processors may be combined to constitute the processing circuitry, and the respective processors may implement the respective functions by executing the programs. The system control function 441, the drive control function 442, the X-ray control function 443, the normal readout function 444, the non-destructive readout function 445, the projection data acquisition function 446, the estimation function 447, the normalization function 448, the correction function 449, the image generation function 450, and the display control function 451 may be respectively referred to as system control circuitry, drive control circuitry, X-ray control circuitry, normal readout circuitry, non-destructive readout circuitry, projection data generator circuitry, estimation circuitry, normalization circuitry, correction circuitry, image generator circuitry, and display control circuitry; and those functions may be implemented as individual hardware circuitry. The above description of the respective functions implemented by the processing circuitry 44 also applies to each of the embodiments and modifications described below.

Also, although the console apparatus 40 is described as an apparatus performing a plurality of functions with a single console, a plurality of functions may be performed by separate apparatuses. For example, the functions of the processing circuitry 44 may be installed dispersively in different apparatuses.

The terminology "processor" used in the above description refers to, for example, circuitry such as a CPU (central processing unit), a GPU (graphics processing unit), an application specific integrated circuit (ASIC), a programmable logic device (such as a simple programmable logic device (SPLD), a complex programmable logic device (CPLD), and a field programmable gate array (FPGA)), etc. If the processor is a CPU, for example, the processor implements its functions by reading and executing the programs stored in the storage circuitry. On the other hand, if the processor is an ASIC, for example, its functions are directly incorporated into the circuitry of the processor as logic circuitry, instead of a program being stored in the storage circuitry. Each processor of the present embodiment is not limited to being configured as single circuitry; multiple sets of independent circuitry may be integrated into a single processor that implements its functions. Furthermore, the multiple components shown in FIG. 1 may be integrated into a single processor to implement its functions. The above description of the "processor" also applies to each embodiment and modification described below.

Also, an apparatus that is constituted by the memory 41, the display 42, the input interface 43, and the projection data acquisition function 446, the estimation function 447, the normalization function 448, the correction function 449, the image generation function 450, and the display control function 451 of the processing circuitry 44 may be referred to as a medical image processing apparatus. Accordingly, the descriptions of the memory 41, the display 42, and the input interface 43, as well as the projection data acquisition function 446, the estimation function 447, the normalization function 448, the correction function 449, the image generation function 450, and the display control function 451 of the processing circuitry 44 apply to descriptions of a medical image processing apparatus. A medical image processing apparatus that is constituted by the memory 41, the display 42, the input interface 43, and the projection data acquisition function 446, the estimation function 447, the normalization function 448, the correction function 449, the image generation function 450, and the display control function 451 of the processing circuitry 44 may be provided as a separate apparatus capable of communicating with the X-ray diagnostic apparatus 1.

With the system control function 441, the processing circuitry 44 controls each of the components of the X-ray diagnostic apparatus 1 based on an input operation received from an operator via the input interface 43. For example, the processing circuitry 44 controls each of the components of the imaging apparatus 10 according to the imaging conditions.

With the drive control function 442, the processing circuitry 44 controls the C-arm driver 142 and the couch driver 32 based on, for example, the information regarding the drive of the C-arm 14 and the top plate 33 input through the input interface 43. The processing circuitry 44 that implements the drive control function 442 is an example of a drive control unit.

With the X-ray control function 443, the processing circuitry 44 reads, for example, the information from the system control function 441, and controls the X-ray conditions, such as a tube current, a tube voltage, a focal-spot size, an irradiation time, a pulse width, etc., of the high-voltage generator 11. The processing circuitry 44 that implements the X-ray control function 443 is an example of an X-ray control unit.

With the normal readout function 444, the processing circuitry 44 causes the X-ray detector 13 to perform normal readout of (i.e., destructively read) signals accumulated in the X-ray detection elements after termination of X-ray exposure. Normal readout is performed after termination of X-ray exposure, that is, between X-ray pulses. The processing circuitry 44 that implements the normal readout function 444 is an example of a second readout unit. The second readout unit may be referred to as a normal readout unit and a destructive readout unit.

With the non-destructive readout function 445, the processing circuitry 44 causes the X-ray detector 13 to non-destructively read signals accumulated in the X-ray detection elements before termination of X-ray exposure. The non-destructive readout is performed before termination of X-ray exposure, that is, during a single X-ray-pulse irradiation. Also, the non-destructive readout is performed at a timing that does not cause saturation according to the type, performance, etc., of the X-ray detector 13. For example, even if the subject P is absent, X-ray conditions and readout timings that do not cause saturation are set. Such X-ray conditions and readout timings can be estimated based on an image level of a Flood acquisition image. The processing circuitry 44 that implements the non-destructive readout function 445 is an example of a first readout unit. The first readout unit may be referred to as a non-destructive readout unit.

With the projection data acquisition function 446, the processing circuitry 44 acquires projection data generated based on detection data read from the X-ray detector 13. At this time, the processing circuitry 44 acquires projection data generated using detection data destructively read by the normal readout function 444 (hereinafter referred to as "a normal readout image") from the aforementioned projection data generator circuitry, and acquires projection data generated using detection data non-destructively read by the non-destructive readout function 445 (hereinafter referred to as "a non-destructive readout image") from the aforementioned projection data generator circuitry. The non-destructive readout image is an example of the first projection data, and the normal readout image is an example of the second projection data. The processing circuitry 44 that implements the projection data acquisition function 446 is an example of an acquisition unit.

With the estimation function 447, the processing circuitry 44 estimates a region in which saturation is occurring (hereinafter referred to as "a saturation region") based on the normal readout image generated by the projection data acquisition function 446. Saturation is a phenomenon in which the detection value of the X-ray detector 13 is saturated when X-rays exceeding the upper limit of the X-ray dose detectable by the X-ray detector 13 enter the X-ray detector 13. In the saturation region, even if X-rays exceeding the upper limit are incident, a value near the upper limit of the X-ray dose is detected as a detection value, preventing detection of a correct value. An example of the method of estimating a saturation region is a method in which a region on the normal readout image that has a signal value exceeding a predetermined threshold is determined to have saturation occurring therein. For example, a value near the upper limit of the X-ray dose detectable by the X-ray detector 13 is used as the predetermined threshold. With the estimation function 447, the processing circuitry 44 also estimates a region in which no saturation is occurring (hereinafter referred to as "a non-saturation region") based on the normal readout image generated by the projection data acquisition function 446. The processing circuitry 44 that implements the estimation function 447 is an example of an estimation unit.

With the normalization function 448, the processing circuitry 44 performs normalization processing on the normal readout image and the non-destructive readout image generated by the projection data acquisition function 446. In the normalization processing, the processing circuitry 44 calculates an X-ray attenuation rate A of the normal readout image and an X-ray attenuation rate A' of the non-destructive readout image, and generates normal normalized data including the X-ray attenuation rate A of the normal readout image and non-destructive normalized data including the X-ray attenuation rate A' of the non-destructive readout image. The X-ray attenuation rate is calculated using a ratio between the intensity of the X-rays that have passed through a subject and the intensity of the X-rays in the absence of a subject. The calculated X-ray attenuation rate is used for the calculation performed in the reconstruction processing.

The X-ray attenuation rate A of the normal readout image is calculated using Formula (1). As shown in Formula (1), the X-ray attenuation rate A of the normal readout image is calculated using an X-ray intensity I of the normal readout image, an X-ray intensity I0 of a Flood image, and a coefficient f. The X-ray intensity I of the normal readout image corresponds to the intensity of the X-rays that have passed through a subject, and the X-ray intensity I0 of the Flood image corresponds to the intensity of the X-rays in the absence of a subject. The Flood image is an image captured in the absence of a subject. The Flood image may be referred to as an "air acquisition image".

$$A = \frac{I}{I_0} * f \qquad (1)$$

The coefficient f is a coefficient for suppressing a gap between the X-ray conditions of the normal readout image and the Flood image. For example, the coefficient f is calculated using Formula (2).

$$f = \frac{kVp(I_0) * mA(I_0) * \sec(I_0)}{kVp(I) * mA(I) * \sec(I)} \qquad (2)$$

In the formula, "kVp" denotes a tube voltage, "mA" denotes a tube current, and "sec" denotes a period of X-ray exposure. If the symbol in the parenthesis is "I", it indicates the X-ray conditions for acquiring the normal readout image. If the symbol in the parenthesis is "I0", it indicates the X-ray conditions for acquiring the Flood image.

It is assumed that the X-ray conditions differ between the X-ray imaging time for generating the Flood image and the X-ray imaging time for generating the normal readout image. Thus, multiplying the ratio between the X-ray intensity I0 of the Flood image and the X-ray intensity I of the normal readout image by the coefficient f makes it possible to suppress the difference in the X-ray conditions.

The X-ray attenuation rate A' of the non-destructive readout image is calculated using Formula (3). As shown in Formula (3), the X-ray attenuation rate A' of the non-destructive readout image is calculated using an X-ray intensity I' of the non-destructive readout image, the X-ray intensity I0 of the Flood image, and a coefficient f'. The X-ray intensity I' of the non-destructive readout image corresponds to the intensity of the X-rays that have passed through a subject, and the X-ray intensity I0 of the Flood image corresponds to the intensity of the X-rays in the absence of a subject.

$$A' = \frac{I'}{I_0} * f' \quad (3)$$

The coefficient f' is a coefficient for resolving a gap between the X-ray conditions of the non-destructive readout image and the Flood image and for aligning the image levels of the normal readout image and the non-destructive readout image. For example, the coefficient f' is calculated using Formula (4). The coefficient f', which is obtained by multiplying the coefficient f used when calculating the X-ray attenuation rate of the normal readout image by the ratio between the image level of the normal readout image and the image level of the non-destructive readout image, is used to align the image intensity of the normal readout image with the image level of the non-destructive readout image. For example, as the image levels of the normal readout image and the non-destructive readout image, an average value of the X-ray intensity in the non-saturation regions of these images can be used.

$$f' = f * \frac{\text{Image level of normal readout}}{\text{Image level of non-destructive readout}} \quad (4)$$

For example, if the X-ray intensity I' of the non-destructive readout image is about half of the X-ray intensity I of the normal readout image, I'≅(½)·I. In this case, the image level of the non-destructive readout image is about half of the image level of the normal readout image; thus, the value of the coefficient f' will be about twice the coefficient f, as shown in Formula (5).

$$f' \approx 2f \quad (5)$$

Also, the X-ray attenuation rate A' of the non-destructive readout image will have a value approximately the same as that of the X-ray attenuation rate A of the normal readout image, as shown in Formula (6).

$$A' \approx \frac{I'}{I_0} * f' \approx \frac{\frac{1}{2}I}{I_0} * 2f \approx \frac{I}{I_0} * f = A \quad (6)$$

In this manner, the X-ray intensity of the non-destructive readout image becomes small as compared to that of the normal readout image; however, multiplying by the ratio of the normal readout image to the non-destructive readout image as a coefficient in the normalization processing performed on the non-destructive readout image makes it possible to calculate non-destructive normalized data whose image level is aligned with the image level of the normal normalized data.

When aligning the image level of the normal readout image with the image level of the non-destructive readout image using the coefficient f', it is also possible to use a ratio between an X-ray accumulation time required when performing the normal readout and an X-ray accumulation time required when performing the non-destructive readout, instead of the ratio between the image level of the normal readout image and the image level of the non-destructive readout image. However, the value of the X-ray accumulation time is a value stored in a system, and there may occur an error between this X-ray accumulation time and the time actually used to accumulate X-rays. Thus, if the ratio of the X-ray accumulation time is used in order to suppress the gap between the image levels of the normal readout image and the non-destructive readout image, there may occur a gap between the result of the normalization processing of the normal readout image and the result of the normalization processing of the non-destructive readout image.

On the other hand, if the ratio between the image level of the normal readout image and the image level of the non-destructive readout image is used in order to suppress the gap between the image levels of the normal readout image and the non-destructive readout image, as shown in Formula (4), the image level of the normal readout image and the image level of the non-destructive readout image can be accurately aligned with each other since a value actually acquired by the X-ray detector 13 is used. If there is no error occurring between the readout time and the actual image level, it is also effective to use a ratio between the X-ray accumulation time required when performing the normal readout and the X-ray accumulation time required when performing the non-destructive readout.

With the correction function 449, the processing circuitry 44 performs saturation correction on the normal readout image. In the saturation correction, the processing circuitry 44 generates corrected data which combines a non-saturation region of the normal normalized data and a saturation region of the non-destructive normalized data (hereinafter the corrected data is referred to as "a saturation-corrected image") by replacing the X-ray attenuation rate A in the saturation region of the normal normalized data with the X-ray attenuation rate A' in the saturation region of the non-destructive normalized data that does not include saturation. The saturation-corrected image is composed of an X-ray attenuation rate that does not include saturation. Since the image level of the non-destructive normalized data is aligned with the image level of the normal normalized data by using the coefficient f' in the normalization processing, the image level of the normal normalized data and the image level of the non-destructive normalized data are aligned with each other in the saturation-corrected image. Processing such as correction of scattered rays, consolidation of radiation quality, etc., may be performed on the saturation-corrected image after the saturation correction is performed. In the present embodiment, the processing circuitry 44 that implements the normalization function 448 and the correction function 449 corresponds to a correction unit.

With the image generation function 450, the processing circuitry 44 performs reconstruction processing on the saturation-corrected image generated by the correction function 449 and generates an X-ray image in which the saturation is corrected. The X-ray image in which the saturation is corrected is, for example, volume data. The processing circuitry 44 may perform various kinds of synthesis processing, subtraction processing, etc., on the generated X-ray image. The processing circuitry 44 that implements the image generation function 450 is an example of an image generator and a reconstruction processing unit.

In the reconstruction processing, Formula (7) is used to calculate a pixel value in each position on the X-ray image using the X-ray attenuation rate of the corrected image generated by the correction function 449. In this formula, "µ" denotes an X-ray attenuation coefficient, and "t" denotes a thickness of a material through which X-rays pass. "AttenuationRate" denotes an X-ray attenuation rate. The tomographic image obtained by the X-ray diagnostic apparatus 1 can also be referred to as a distribution of the X-ray attenuation coefficient µ.

$$\mu t = \log \frac{1}{AttenuationRate} \quad (7)$$

With the display control function 451, the processing circuitry 44 reads a signal from the system control function 441, and acquires a desired X-ray image from the memory 41 to be displayed on the display 42. The processing circuitry 44 that implements the display control function 451 is an example of a display controller.

Next, the operation of the X-ray diagnostic apparatus 1 according to the present embodiment will be described. The process procedure described below is a mere example, and each step may be changed to the extent possible. Omission, replacement, or addition of a step in the process procedure described below can be made as appropriate according to the manner in which the present embodiment will be realized.

Figure 2:
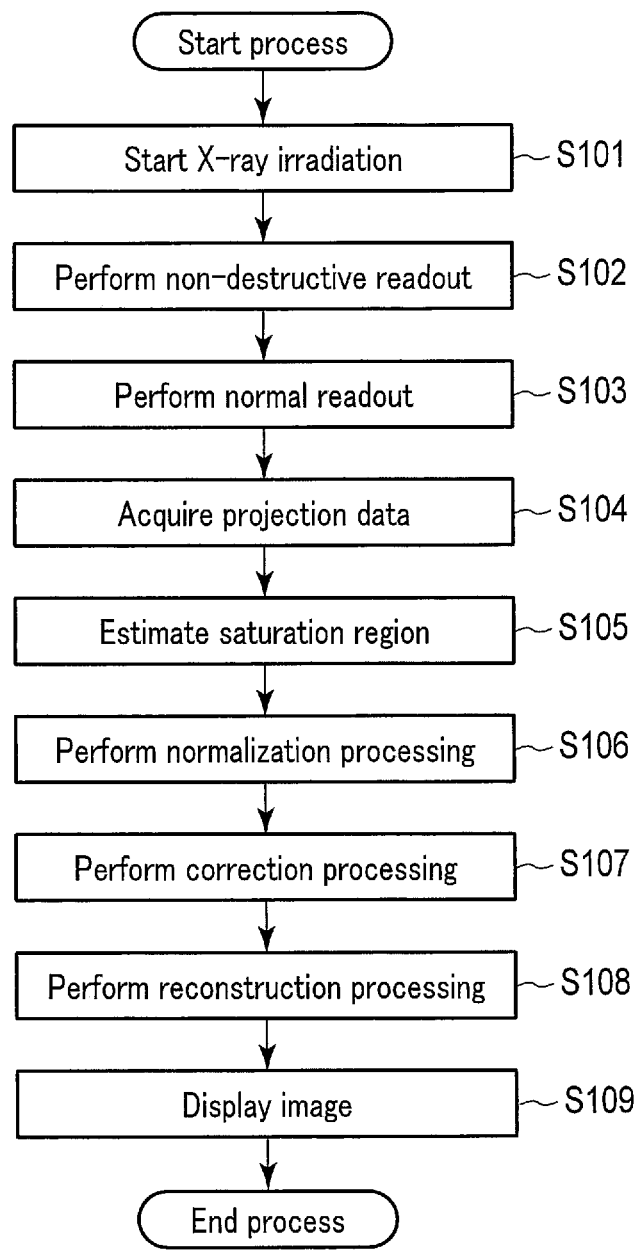
FIG. 2 is a flowchart illustrating procedures of an image generating process performed by the X-ray diagnostic apparatus according to the embodiment.

FIG. 2 is a flowchart showing an example of a procedure of an image generating process performed by the processing circuitry 44 according to the present embodiment. The image generating process is a process of generating an X-ray image of a subject P by irradiating the subject P with X-ray pulses and detecting X-rays that have passed through the subject P. The image generating process is also a process of generating a saturation-corrected image by performing saturation correction on a normal readout image using a non-destructive readout image. Hereinafter, a process of generating an X-ray image for a single X-ray-pulse exposure will be described as an example. The image generating process is started in a state where there is no signal in the X-ray detection elements after normal readout relating to the immediately preceding X-ray pulse exposure is completed and then the accumulation of electric charge signals in the X-ray detector 13 is reset.

Figure 3:
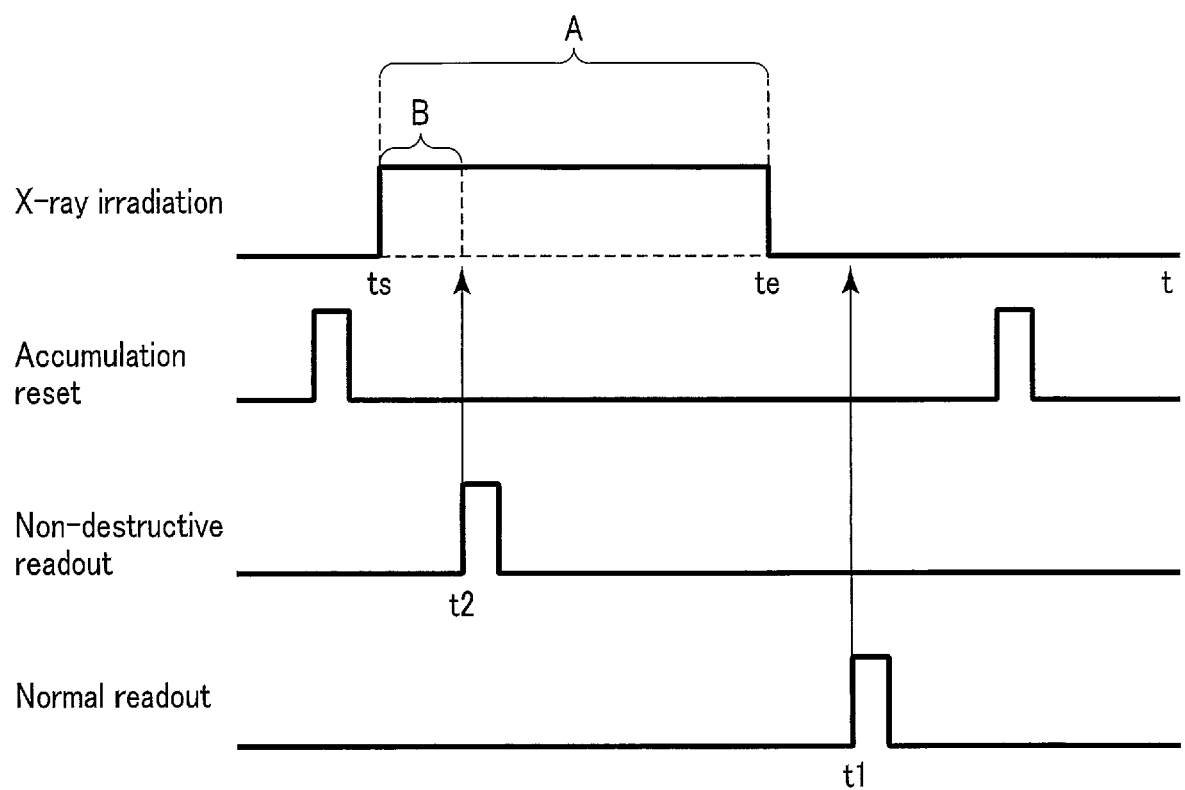
FIG. 3 is a diagram for explaining a timing of signal readout performed by the X-ray diagnostic apparatus according to the embodiment through the image generating process.
Figure 4:
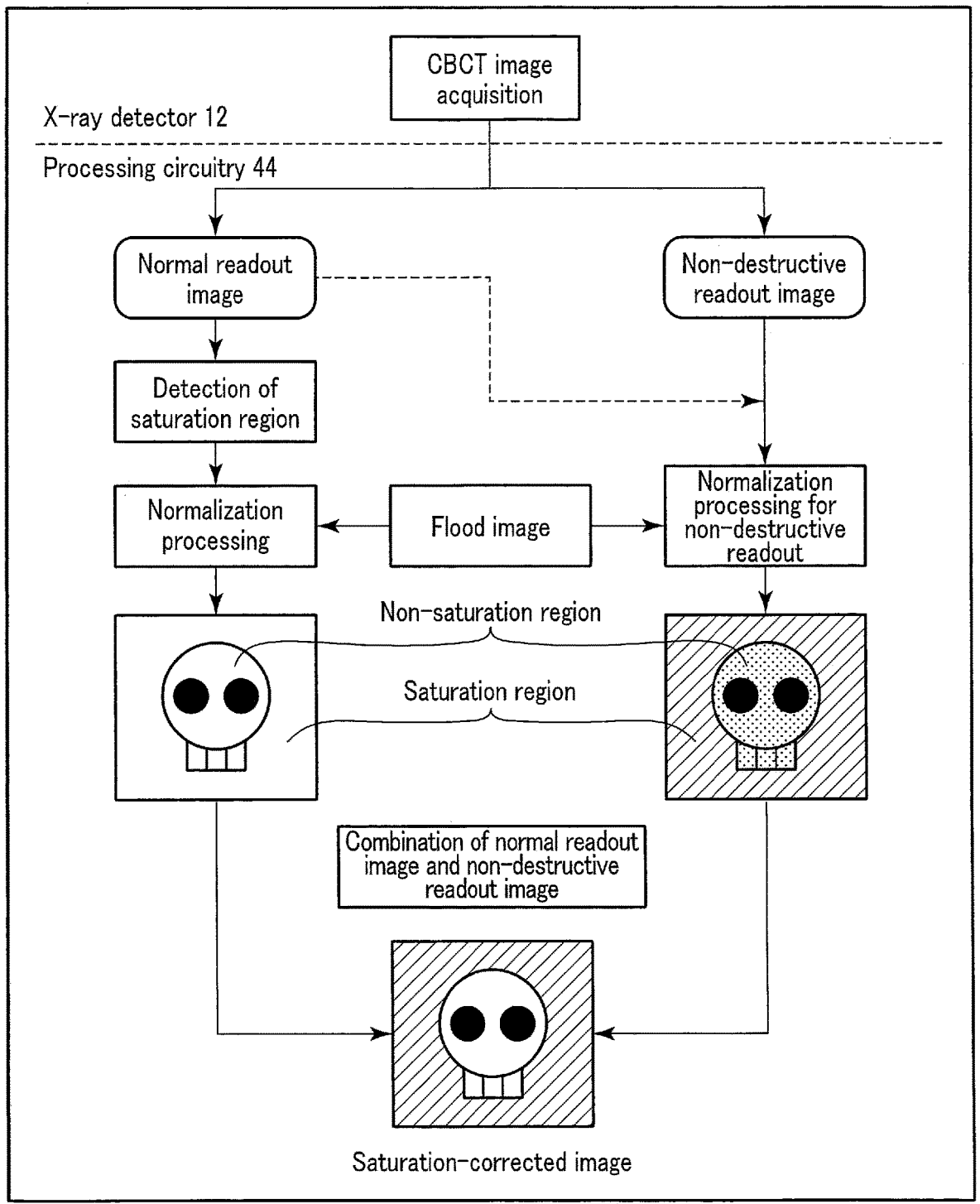
FIG. 4 is a diagram for explaining a flow of a process performed until a saturation-corrected image is generated by the X-ray diagnostic apparatus according to the embodiment through the image generating process.

FIG. 3 is a diagram for explaining a timing of signal readout performed by the image generating process. The horizontal axis in FIG. 3 represents time. FIG. 3 shows a process ranging from performance of a single X-ray-pulse irradiation after resetting of the accumulation of the electric charge signals in the X-ray detector 13 to resetting of the signals accumulated by the X-ray pulses after termination of the X-ray pulse exposure. Herein, the time at which normal readout is performed (hereinafter referred to as a "normal readout time") is defined as t1, and the time at which non-destructive readout is performed (hereinafter referred to as a "non-destructive readout time") is defined as t2. FIG. 4 is a diagram for explaining a flow of a process performed until a saturation-corrected image is generated by the image generating process.

(Image Generating Process)
(Step S101)
With the system control function 441, the drive control function 442, and the X-ray control function 443, the processing circuitry 44 performs X-ray imaging using the imaging apparatus 10. At this time, the processing circuitry 44 starts X-ray pulse emission from the X-ray generator 12 at an X-ray pulse irradiation start time ts. The emitted X-rays are continuously applied until an irradiation end time te. In this manner, the subject P is irradiated with X-rays during a time period A from the irradiation start time ts to the irradiation end time te. The time period A corresponds to the X-ray accumulation time required when performing the normal readout.

(Step S102)
Next, with the non-destructive readout function 445, the processing circuitry 44 non-destructively reads signals accumulated in the X-ray detection elements from the X-ray detector 13 at a non-destructive readout time t2. At this time, signals accumulated during a time period B from the irradiation start time ts to the non-destructive readout time t2 are read. The time period B corresponds to the X-ray accumulation time required when performing the non-destructive readout. Since the signals accumulated in the X-ray detection elements during the time period B are non-destructively read, the signals accumulated in the X-ray detection elements are retained without being erased even after the non-destructive readout is performed. The non-destructive readout time t2 is set at a time between the irradiation start time ts and the irradiation end time te. Thus, the signals accumulated in the X-ray detection elements are read from the X-ray detector 13 before termination of X-ray exposure, that is, during a single X-ray-pulse irradiation. The non-destructive readout time t2 is set in advance at a time that does not cause saturation according to the type, performance, etc., of the X-ray detector 13.

(Step S103)
Next, with the normal readout function 444, the processing circuitry 44 normally reads signals accumulated in the X-ray detection elements from the X-ray detector 13 at a normal readout time t1. At this time, signals accumulated during the time period A from the irradiation start time ts to the irradiation end time te are read. Since the signals accumulated in the X-ray detection elements are destructively read, the signals accumulated in the X-ray detection elements are erased. The normal readout time t1 is set at a time after the irradiation end time te. Thus, the signals accumulated in the X-ray detection elements are read from the X-ray detector 13 after termination of X-ray exposure, that is, after a single X-ray-pulse irradiation. Also, saturation may be generated in the signals read by the normal readout function 444.

(Step S104)
Next, the processing circuitry 44 implements the projection data acquisition function 446. With the projection data acquisition function 446, the processing circuitry 44 acquires, from the projection data generator circuitry, a normal readout image generated based on detection data acquired through the normal readout in the processing of step S103, and acquires, from the projection data generator circuitry, a non-destructive readout image generated based on detection data acquired through the non-destructive readout in the processing of step S102. The normal readout image includes saturation. On the other hand, the non-destructive readout image does not include saturation. For example, the normal readout image and the non-destructive readout image that are generated are stored in the memory 41.

(Step S105)

Next, with the estimation function 447, the processing circuitry 44 estimates a saturation region and a non-saturation region based on the normal readout image acquired in the processing of step S104.

(Step S106)

Next, with the normalization function 448, the processing circuitry 44 performs normalization processing on each of the normal readout image and the non-destructive readout image and generates normal normalized data and non-destructive normalized data. At this time, the processing circuitry 44 performs normalization processing so as to align the image level of the normal readout image with the image level of the non-destructive readout image.

(Step S107)

Next, with the correction function 449, the processing circuitry 44 performs saturation correction on the normal readout image. In the saturation correction, the processing circuitry 44 replaces the saturation region of the normal readout image using the saturation region of the non-destructive readout image. In other words, the processing circuitry 44 generates a corrected image which combines the X-ray attenuation rate of the normal normalized data in the saturation region and the X-ray attenuation rate of the non-destructive normalized data in the non-saturation region.

(Step S108)

Next, with the image generation function 450, the processing circuitry 44 implements reconstruction processing. In the reconstruction processing, the processing circuitry 44 performs reconstruction processing on the corrected image generated in the processing of step S107 and thereby generates an X-ray image. The X-ray image is, for example, volume data. The X-ray image generated does not include saturation since a pixel value calculated using the non-destructive readout image is used for the pixel value of the saturation region. For example, the X-ray image generated is stored in the memory 41.

(Step S109)

With the image generation function 450, the processing circuitry 44 generates, based on the x-ray image, tomographic image data, three-dimensional image data, and the like to be displayed on the display 42. The processing circuitry 44 causes the memory 41 to store the generated tomographic image data, three-dimensional image data, and the like. The processing circuitry 44 then implements the display control function 451. With the display control function 451, the processing circuitry 44 causes the display 42 to display the tomographic image data, the three-dimensional image data, and the like as X-ray images.

By repeating the process from step S101 to step S109 each time X-ray pulse irradiation is performed, the processing circuitry 44 generates a saturation-corrected X-ray image whenever necessary, and causes the display 42 to display the generated X-ray image.

Hereinafter, the advantageous effects of the X-ray diagnostic apparatus 1 as a medical image diagnosis apparatus according to the present embodiment will be explained.

The X-ray diagnostic apparatus 1 of the present embodiment can cause the X-ray detector 13 to non-destructively read signals accumulated in the X-ray detection elements before termination of X-ray exposure, cause the X-ray detector 13 to destructively read the signals after termination of X-ray exposure, acquire a non-destructively readout image generated based on the non-destructively read signals, acquire a normal readout image generated based on the destructively read signals, estimate a saturation region in which saturation is occurring based on the normal readout image, and replace a signal in the saturation region of the normal readout image with a signal in the saturation region of the non-destructive readout image. The non-destructive readout image is an example of the first projection data, and the normal readout image is an example of the second projection data.

With the above configuration, the X-ray diagnostic apparatus 1 of the present embodiment can perform accurate saturation correction by acquiring a non-destructive readout image that does not cause saturation using the X-ray detector 13 having the non-destructive readout function and correcting a saturation region of the normal readout image using the acquired non-destructive readout image as an image for correction. That is, by detecting the saturation region of the normal readout image and replacing the region with a non-destructive readout image having no saturation, it is possible to perform reconstruction processing on data having no saturation, making it possible to generate a reconstructed image with no artifacts caused by saturation. Generating a reconstructed image with no artifacts makes it easy for a user to perform diagnosis.

Also, the X-ray diagnostic apparatus 1 as a medical image diagnosis apparatus according to the present embodiment can replace the signal of the normal readout image in a state where the image level of the non-destructive readout image is aligned with the image level of the normal readout image.

Specifically, the image level of the non-destructive readout image is aligned with the image level of the normal readout image by converting the X-ray attenuation rate of the non-destructive readout image. For example, it is possible to align the image level of the non-destructive readout image with the image level of the normal readout image using the coefficient f' including the ratio between the image level of the non-destructive readout image and the image level of the normal readout image, as shown in Formulas (3) and (4).

According to the above configuration, aligning the image level of the non-destructive readout image with the image level of the normal readout image makes it possible to generate an X-ray image with no artifacts caused by saturation and with a difference between the image levels of the saturation region and the non-saturation region suppressed.

In addition, since a value actually acquired by the X-ray detector 13 is used by adopting the ratio between the image level of the normal readout image and the image level of the non-destructive readout image, it is possible to suppress a gap between the results of the normalization processing performed on the normal readout image and the non-destructive readout image.

(First Modification)

A first modification will be described. This modification is a modification of the configuration of the embodiment described below. Descriptions of the configuration, operation, and effect that are the same as those of the embodiment will be omitted.

In the above-described embodiment, a coefficient for aligning the image levels of the normal readout image and the non-destructive readout image is used for calculating the X-ray attenuation rate A' of the non-destructive readout image using the normalization function 448. Then, saturation correction is performed using the result of the normalization processing performed on the normal readout image and the result of the normalization processing performed on the non-destructive readout image. On the other hand, in the present modification, saturation correction is performed using the normal readout image and the non-destructive readout image before the normalization processing is performed.

With the correction function 449, the processing circuitry 44 performs saturation correction on the normal readout image using the saturation region of the non-destructive readout image. In the saturation correction, the processing circuitry 44 first performs correction to align the image levels of the normal readout image and the non-destructive readout image, thereby generating a non-destructive readout image corrected to have the same image level as the image level of the normal readout image (hereinafter the non-destructive readout image is referred to as "a corrected image of a non-destructive readout image"). An example of the method of aligning the image levels of the normal readout image and the non-destructive readout image is to perform correction in which the non-destructive readout image is multiplied by a ratio between the image level of the normal readout image and the image level of the non-destructive readout image. In this case, the image levels of the normal readout image and the non-destructive readout image are aligned with each other by converting the image level of the non-destructive readout image. Alternatively, the non-destructive readout image may be multiplied by a ratio between the X-ray accumulation time required when performing the normal readout and the X-ray accumulation time required when performing the non-destructive readout, instead of the ratio between the image level of the normal readout image and the image level of the non-destructive readout image.

With the correction function 449, the processing circuitry 44 generates a composite image which combines a non-saturation region of the normal readout image and a saturation region of the non-destructive readout image by replacing a signal in the saturation region of the normal readout image with a signal in the saturation region of the non-destructive normalized data that does not include saturation. The composite image is composed of signals that do not include saturation. In the present modification, the processing circuitry 44 that implements the correction function 449 is an example of a correction unit.

With the normalization function 448, the processing circuitry 44 performs normalization processing on the composite image generated by the correction function 449. In the normalization processing, the processing circuitry 44 calculates an X-ray attenuation rate of the composite image and generates normalized data that includes the X-ray attenuation rate of the composite image. The X-ray attenuation rate of the composite image is calculated using a ratio between an X-ray intensity of the composite image and an X-ray intensity of a Flood image and a coefficient for suppressing a gap between the X-ray conditions of the composite readout image and the Flood image, as in the case of using Formula (1) for the X-ray attenuation rate A of the normal readout image described above. For example, the X-ray conditions for the normal readout can be used as the X-ray conditions of the composite readout image.

With the image generation function 450, the processing circuitry 44 performs the above-described reconstruction processing on the composite image generated by the normalization function 448 and generates a saturation-corrected image.

Figure 5:
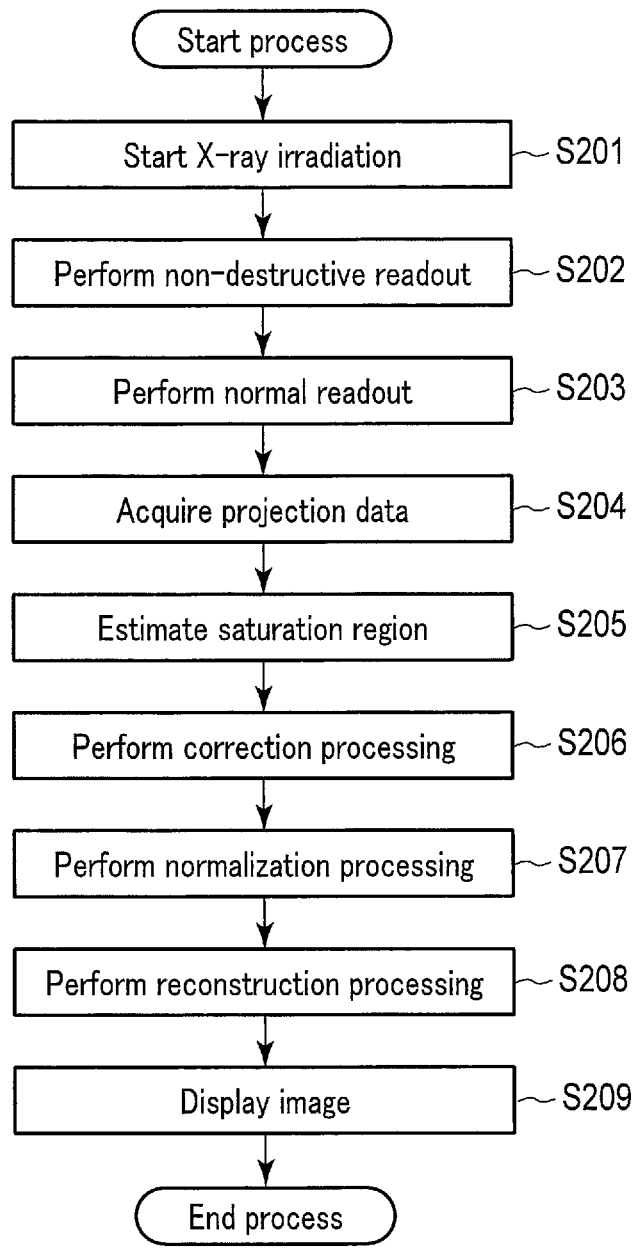
FIG. 5 is a flowchart illustrating procedures of an image generating process performed by an X-ray diagnostic apparatus according to a first modification.
Figure 6:
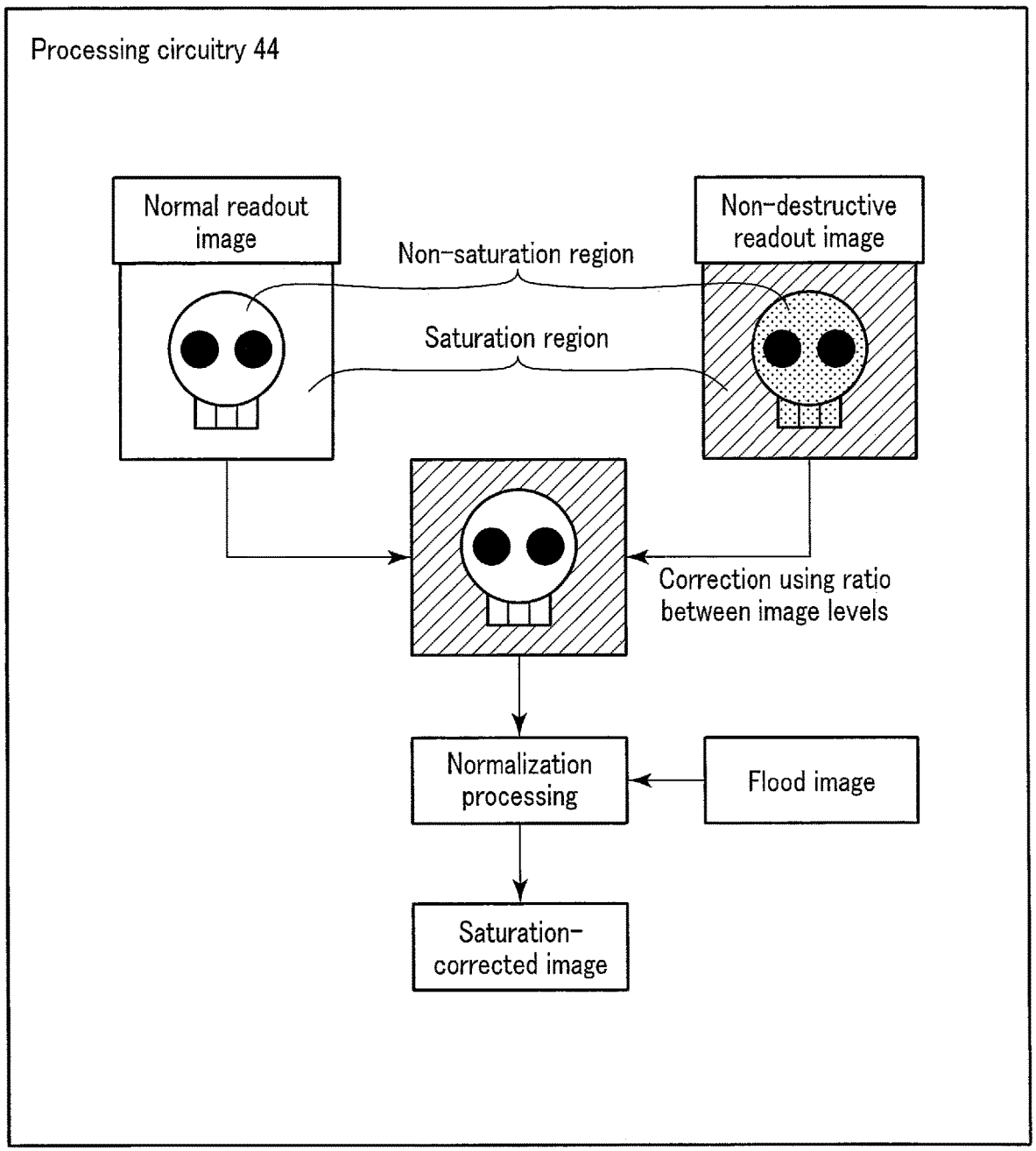
FIG. 6 is a diagram for explaining a flow of a process performed until a saturation-corrected image is generated by the X-ray diagnostic apparatus according to the first modification through the image generating process.

FIG. 5 is a flowchart showing an example of a procedure of an image generating process performed by the processing circuitry 44 according to the present modification. Since the processing of steps S201 to S205 and step S209 are the same as the processing of steps S101 to S105 and step S109 in FIG. 2, respectively, descriptions thereof will be omitted. FIG. 6 is a diagram for explaining a flow of a process performed until a saturation-corrected image is generated by the image generating process.

(Image Generating Process)
(Step S206)

With the correction function 449, the processing circuitry 44 performs saturation correction on the normal readout image. In the saturation correction, the processing circuitry 44 first performs correction in which the non-destructive readout image is multiplied by a ratio between the image level of the normal readout image and the image level of the non-destructive readout image, thereby generating a corrected image of the non-destructive readout image. Next, the processing circuitry 44 generates a composite image which combines a saturation region of the normal readout image and a non-saturation region of the non-destructive readout image by replacing the saturation region of the normal readout image using the saturation region of the non-destructive readout image.

(Step S207)

Next, with the normalization function 448, the processing circuitry 44 performs normalization processing on the composite image generated in the processing of step S206 and generates normalized data.

(Step S208)

Next, with the image generation function 450, the processing circuitry 44 performs reconstruction processing on the normalized data generated in the processing of step S207 and thereby generates an X-ray image. The X-ray image generated does not include saturation since a pixel value calculated using the non-destructive readout image is used for the pixel value of the saturation region. For example, the X-ray image generated is stored in the memory 41.

Hereinafter, the advantageous effects of the X-ray diagnostic apparatus 1 as a medical image diagnosis apparatus according to the present modification will be explained.

The X-ray diagnostic apparatus 1 of the present modification can align the image level of the non-destructive readout image with the image level of the normal readout image by converting the image level of the non-destructive readout image. The non-destructive readout image is an example of the first projection data, and the normal readout image is an example of the second projection data.

In the above-described embodiment, a coefficient for aligning the image level of the non-destructive readout image with the image level of the normal readout image is used in the normalization processing performed on the non-destructive readout image. Thus, it is necessary to perform normalization processing on the normal readout image and the non-destructive readout image using different formulas for each of the images. On the other hand, in the present modification, it is possible to perform normalization processing on the normal readout image and the non-destructive readout image without using different formulas for each of the images by subjecting, prior to performance of the normalization processing, the non-destructive readout image to saturation correction including correction to align the image levels of the normal readout image and the non-destructive readout image.

(Second Modification)

When calculating the X-ray attenuation rate A' of the non-destructive readout image in the normalization processing, it is possible to use an X-ray intensity of a Flood image captured in the absence of a subject and generated through the non-destructive readout, instead of using the X-ray intensity I0 of the Flood image, in order to align the image levels of the normal readout image and the non-destructive readout image. In this case, the same coefficient f as that used in the normalization processing performed on the normal readout image can be used instead of the coefficient f' since using an X-ray intensity of the Flood image generated through the non-destructive readout allows for suppression of a gap between the image levels of the normal readout image and the non-destructive readout image.

(Third Modification)

A third modification will be described. This modification is a modification of the configuration of the embodiment described below. Descriptions of the configuration, operation, and effect that are the same as those of the embodiment will be omitted. In the above-described embodiment, the same coefficient f' is used in all positions in the normalization processing performed on the non-destructive readout image. During the non-destructive readout, readout from a plurality of X-ray detection elements is sequentially performed during X-ray irradiation; thus, there may occur a lag in the X-ray accumulation time depending on the X-ray detection element. Therefore, the non-destructive readout image has unevenness in the image level caused by the lag in the X-ray accumulation time depending on the pixel. In the present modification, normalization processing is performed by dividing the non-destructive readout image into multiple regions and using different coefficients, respectively, for the multiple regions obtained by dividing the image.

With the normalization function 448, the processing circuitry 44 first divides the non-destructive readout image into multiple regions having different readout timings (hereinafter referred to as "readout regions"). Next, the processing circuitry 44 performs normalization processing using different coefficients f', respectively, for the multiple readout regions obtained by dividing the image. For example, in Formula (4) of the coefficient f' described above, an average value of the image levels of the respective readout regions is used as the image level of the non-destructive readout image. Then, the normalization processing is performed using different values as the image level of the non-destructive readout image, respectively, for the multiple readout regions. This allows the image level of the non-destructive readout image to be aligned with the image level of the normal readout image for each readout region.

In the present modification, it is possible to suppress the unevenness in the image level caused by the difference in the readout timing at the time of acquiring the non-destructive readout image by performing the normalization processing for each of the multiple readout regions having different readout timings.

(Fourth Modification)

A fourth modification will be described. This modification is a modification of the configuration of the embodiment described below. Descriptions of the configuration, operation, and effect that are the same as those of the embodiment will be omitted.

In the present modification, a detector capable of performing non-destructive readout multiple times during a single X-ray exposure is used as the X-ray detector 13.

With the non-destructive readout function 445, the processing circuitry 44 performs pre-set non-destructive readout multiple times during a single X-ray-pulse irradiation. The processing circuitry 44 acquires a non-destructive readout image generated using detection data detected through the non-destructive readout performed multiple times. A method of generating a non-destructive readout image will be described later.

Figure 7:
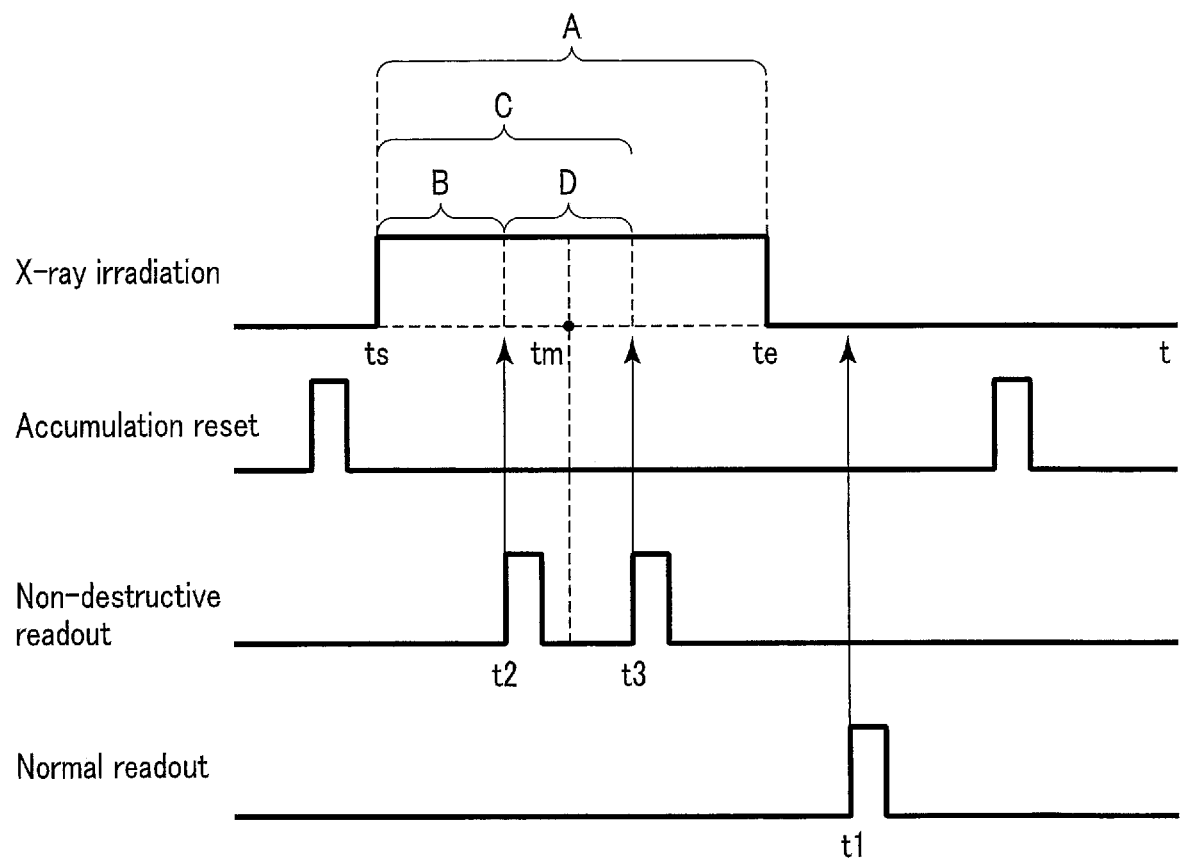
FIG. 7 is a diagram for explaining a timing of signal readout performed by an X-ray diagnostic apparatus according to a fourth modification through an image generating process.

FIG. 7 is a diagram for explaining a timing of signal readout performed by the image generating process in the present modification. The horizontal axis in FIG. 7 represents time. FIG. 7 shows a process ranging from performance of a single X-ray-pulse irradiation after resetting of the accumulation of the electric charge signals in the X-ray detector 13 to resetting of the signals accumulated by the X-ray pulses after termination of the X-ray pulse exposure.

Herein, a case of performing non-destructive readout at a first readout time t2 and a second readout time t3 during a single X-ray-pulse irradiation will be illustrated. The second readout time t3 is after the first readout time t2. The first readout time t2 and the second readout time t3 are based on the irradiation start time ts and are set in advance.

When the non-destructive readout is performed at the first readout time t2, the signals accumulated during a time period B from the irradiation start time ts to the first readout time t2 are read. At this time, since the signals accumulated in the X-ray detection elements are non-destructively read, the signals accumulated in the X-ray detection elements are retained without being erased even after the non-destructive readout is performed.

When the non-destructive readout is performed at the second readout time t3, the signals accumulated during a time period C from the irradiation start time ts to the second readout time t3 are read. At this time, since the signals accumulated in the X-ray detection elements are non-destructively read, the signals accumulated in the X-ray detection elements are retained without being erased even after the non-destructive readout is performed.

Also, the first readout time t2 and the second readout time t3 are set at the boundary times created by dividing the time period A from the X-ray pulse irradiation start time ts to the irradiation end time te into three segments. That is, the time period B from the irradiation start time ts to the first readout time t2, the time period D from the first readout time t2 to the second readout time t3, and the time period (A-C) from the second readout time t3 to the irradiation end time te are approximately the same. The central time between the first readout time t2 and the second readout time t3 coincides with the central time between the X-ray exposure irradiation start time ts and the X-ray exposure irradiation end time te. That is, the first readout time t2 and the second readout time t3 are set so that they are respectively deviated away from the central time tm of the X-ray exposure by the same amount of time. It suffices that the first readout time t2 and the second readout time t3 are set so that they are respectively deviated away from the central time tm of the X-ray exposure by the same amount of time.

The processing circuitry 44 acquires a non-destructive readout image generated using data obtained by subtracting the detection data read at the first readout time t2 from the detection data read at the second readout time t3. The non-destructive readout image serves as projection data that includes the signals accumulated during the time period D from the first readout time t2 to the second readout time t3.

In the above-described embodiment, the lag in the readout timing or the wobbling of the X-ray detector 13 and the like occurring at the time of rotational acquisition may cause misalignment of an object during the time period from the X-ray pulse irradiation start time to the X-ray pulse irradiation end time. In this case, the central position of the object in the non-destructive readout image and the central position of the object in the normal readout image may be shifted depending on the non-destructive readout timing.

On the other hand, the present modification allows for acquisition of a non-destructive image corresponding to the X-rays accumulated at the timing that matches the central timing of the X-ray irradiation time by performing, multiple times, the non-destructive readout set at the timing deviated from the central time tm of the X-ray exposure by the same amount of time and acquiring a non-destructive readout image generated using the difference between the read detection data. As a result, deviation of the central position of the object in the non-destructive image with respect to the normal readout image is inhibited.

(Fifth Modification)

A fifth modification will be described. This modification is a modification of the configuration of the embodiment described below. Descriptions of the configuration, operation, and effect that are the same as those of the embodiment will be omitted.

In the present modification, the processing circuitry 44 implements the correction function 449, and replaces, in a saturation-corrected image in which a saturation region of normal normalized data is replaced with non-destructive normalized data, the X-ray attenuation rate of the region near the boundary between the saturation region and the non-saturation region (hereinafter the region near the boundary is referred to as "a boundary region") with a value obtained by combining the X-ray attenuation rate A of the normal normalized data with the X-ray attenuation rate A' of the non-destructive normalized data. For example, the X-ray attenuation rate of the boundary region is replaced with a value obtained by combining the X-ray attenuation rate A of the normal normalized data with the X-ray attenuation rate A' of the non-destructive normalized data at a predetermined ratio. For example, if the inner side of the boundary is the non-saturation region and the outer side of the boundary is the saturation region, the X-ray attenuation rate in a position slightly inside the boundary is set as a value that uses the X-ray attenuation rate A of the normal normalized data as-is, and the ratio of combining the X-ray attenuation rate A of the normal normalized data with the X-ray attenuation rate A' of the non-destructive normalized data is increased as it approaches the outer side of the boundary.

In the above-described embodiment, the lag in the readout timing or the wobbling of the X-ray detector 13 and the like occurring at the time of rotational acquisition may cause discontinuity of the signal value at the boundary section between the saturation region and the non-saturation region. On the other hand, in the present modification, a saturation-corrected image with a smooth boundary can be generated by providing a boundary region used by combining the X-ray attenuation rate A of the normal normalized data and the X-ray attenuation rate A' of the non-destructive normalized data at a predetermined ratio when replacing the saturation region of the normal readout image with the saturation region of the non-destructive readout image.

(Sixth Modification)

An X-ray image may be generated by performing the normal readout and the non-destructive readout described above every time the C-arm 14 rotates at a predetermined angle and performing the saturation correction described above using the normal readout image and the non-destructive readout image read for each predetermined rotational angle. In this case, the multiple non-destructive readout images generated for each predetermined rotational angle are, for example, subjected to the normalization processing using different coefficients f', so that the image levels of the non-destructive readout image and the normal readout image are aligned with each other.

OTHER EMBODIMENTS

The functions of the embodiment, etc., described above may be installed in a separate apparatus from the X-ray diagnostic apparatus 1. For example, these functions may be realized in a medical image processing apparatus provided with processing circuitry configured to acquire the detection data output from the X-ray detector 13 of the X-ray diagnostic apparatus 1 and perform the projection data acquisition function 446, the estimation function 447, the normalization function 448, the correction function 449, the image generation function 450, and the display control function 451 on the acquired detection data. In this case as well, the same effects as those achieved by the embodiment, modifications, etc., described above can be achieved.

According to at least one embodiment described above, it is possible to generate a medical image in which artifacts caused by saturation are reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising processing circuitry configured to:
   cause an X-ray detector to read a signal in a non-destructive readout before termination of X-ray exposure, the signal being accumulated in an X-ray detection element;
   cause the X-ray detector to read the signal in a destructive readout after termination of X-ray exposure;
   acquire first projection data generated based on the signal read in the non-destructive readout and acquire second projection data generated based on the signal read in the destructive readout;
   estimate, based on the second projection data, a saturation region in which saturation is occurring; and
   replace a signal in the saturation region of the second projection data with a signal in the saturation region of the first projection data.

2. The X-ray diagnostic apparatus according to claim 1, wherein the processing circuitry is configured to replace the signal of the second projection data in a state where an image level of the first projection data and an image level of the second projection data are aligned with each other.

3. The X-ray diagnostic apparatus according to claim 2, wherein the processing circuitry is configured to align the image level of the first projection data with the image level of the second projection data by converting an X-ray attenuation rate of the first projection data.

4. The X-ray diagnostic apparatus according to claim 2, wherein the processing circuitry is configured to align the image level of the first projection data with the image level of the second projection data by calculating an X-ray attenuation rate of the second projection data using an air acquisition image generated by performing non-destructive readout in an absence of a subject.

5. The X-ray diagnostic apparatus according to claim 2, wherein the processing circuitry is configured to align the image level of the first projection data with the image level of the second projection data by converting the image level of the first projection data.

6. The X-ray diagnostic apparatus according to claim 2, wherein the processing circuitry is configured to align the image level of the first projection data with the image level of the second projection data using a ratio between the image level of the first projection data and the image level of the second projection data.

7. The X-ray diagnostic apparatus according to claim 2, wherein the processing circuitry is configured to align the image level of the first projection data with the image level of the second projection data using a ratio between an X-ray accumulation time required when reading the first projection data and an X-ray accumulation time required when reading the second projection data.

8. The X-ray diagnostic apparatus according to claim 2, wherein the processing circuitry is configured to divide the saturation region into multiple regions whose readout timings differ from each other, and align the image level of the first projection data with the image level of the second projection data for each of the multiple regions.

9. The X-ray diagnostic apparatus according to claim 1, wherein
the processing circuitry is configured to perform the non-destructive readout at each of a first readout time and a second readout time following the first readout time, and
a central time between the first readout time and the second readout time coincides with a central time between a time of starting X-ray exposure and a time of ending X-ray exposure.

10. The X-ray diagnostic apparatus according to claim 1, wherein the processing circuitry is configured to:
further estimate, based on the first projection data, a non-saturation region in which no saturation is occurring; and
replace a signal near a boundary between the saturation region and the non-saturation region of the second projection data with a signal obtained by combining the signal of the first projection data with the signal of the second projection data.

11. The X-ray diagnostic apparatus according to claim 10, wherein the processing circuitry is configured to change, according to a distance from the boundary, a ratio at which the signal of the first projection data is combined with the signal of the second projection data.

12. The X-ray diagnostic apparatus according to claim 1, wherein the processing circuitry is further configured to perform reconstruction processing on the replaced second projection data and generate three-dimensional image data.

13. The X-ray diagnostic apparatus according to claim 1 further comprising a support arm configured to hold an X-ray tube configured to emit X-rays and the X-ray detector,
wherein the processing circuitry is configured to:
acquire the first projection data and the second projection data sequentially acquired while the X-ray detector is rotated around a subject by the support arm; and
replace a signal in the saturation region of the second projection data with a signal in the saturation region of the first projection data for each rotational angle of the support arm.

14. A medical image processing apparatus comprising processing circuitry configured to:
acquire first projection data generated based on a signal read in non-destructive readout from an X-ray detection element before termination of X-ray exposure, and acquire second projection data generated based on a signal read in destructive readout from the X-ray detection element after termination of X-ray exposure;
estimate, based on the second projection data, a saturation region in which saturation is occurring; and
replace a signal in the saturation region of the second projection data with a signal in the saturation region of the first projection data.

15. The medical image processing apparatus according to claim 14, wherein the processing circuitry is configured to replace the signal of the second projection data in a state where an image level of the first projection data and an image level of the second projection data are aligned with each other.

16. The medical image processing apparatus according to claim 15, wherein the processing circuitry is configured to align the image level of the first projection data with the image level of the second projection data by converting an X-ray attenuation rate of the first projection data.

17. The medical image processing apparatus according to claim 15, wherein the processing circuitry is configured to align the image level of the first projection data with the image level of the second projection data by converting the image level of the first projection data.

18. The medical image processing apparatus according to claim 15, wherein the processing circuitry is configured to align the image level of the first projection data with the image level of the second projection data using a ratio between the image level of the first projection data and the image level of the second projection data.

19. The medical image processing apparatus according to claim 14, wherein the processing circuitry is further configured to perform reconstruction processing on the replaced second projection data and generate three-dimensional image data.

20. A non-transitory computer-readable storage medium storing a program for causing a computer to execute:
a function to cause an X-ray detector to read a signal in a non-destructive readout before termination of X-ray exposure, the signal being accumulated in an X-ray detection element;
a function to cause the X-ray detector to read the signal in a destructive readout after termination of X-ray exposure;
a function to acquire first projection data generated based on the signal read in the non-destructive readout and acquire second projection data generated based on the signal read in the destructive readout;
a function to estimate, based on the second projection data, a saturation region in which saturation is occurring; and
a function to replace a signal in the saturation region of the second projection data with a signal in the saturation region of the first projection data.

* * * * *